United States Patent
Grimes et al.

(10) Patent No.: US 10,994,310 B2
(45) Date of Patent: May 4, 2021

(54) LIQUID-DISPENSING, EFFLUENT SHIELDING AND MICROBE ELIMINATING METHODS

(71) Applicants: W. Reid Grimes, Shreveport, LA (US); Marian D. Grimes, Shreveport, LA (US); William Reid Grimes, Jr., Shreveport, LA (US)

(72) Inventors: W. Reid Grimes, Shreveport, LA (US); Marian D. Grimes, Shreveport, LA (US); William Reid Grimes, Jr., Shreveport, LA (US)

( * ) Notice: Subject to any disclaimer, the term of this patent is extended or adjusted under 35 U.S.C. 154(b) by 0 days.

(21) Appl. No.: 16/896,412

(22) Filed: Jun. 9, 2020

(65) Prior Publication Data
US 2020/0298285 A1 Sep. 24, 2020

Related U.S. Application Data

(62) Division of application No. 14/710,686, filed on May 13, 2015.

(51) Int. Cl.
*B08B 3/02* (2006.01)
*B08B 3/08* (2006.01)
*A61L 2/18* (2006.01)

(52) U.S. Cl.
CPC .............. *B08B 3/02* (2013.01); *A61L 2/18* (2013.01); *B08B 3/08* (2013.01); *A61L 2202/15* (2013.01)

(58) Field of Classification Search
None
See application file for complete search history.

(56) References Cited

U.S. PATENT DOCUMENTS

| | | |
|---|---|---|
| 5,004,119 A | 4/1991 | Irwin |
| 5,419,077 A | 5/1995 | Tombarelli |
| 5,496,290 A | 3/1996 | Ackerman |
| 5,497,516 A | 3/1996 | Irwin |
| 5,833,675 A | 11/1998 | Garcia |
| 6,050,981 A | 4/2000 | Lampropoulos et al. |
| 6,443,368 B1 | 9/2002 | Kohls |
| 6,637,151 B1 | 10/2003 | Tillman |
| 7,431,222 B2 | 10/2008 | Monterrosa |
| 7,913,932 B2 | 3/2011 | Wu |
| 8,002,757 B1 | 8/2011 | Schultz |

(Continued)

*Primary Examiner* — Mikhail Kornakov
*Assistant Examiner* — Pradhuman Parihar
(74) *Attorney, Agent, or Firm* — R. Keith Harrison

(57) ABSTRACT

A method of eliminating microbes in an overflow space in a sink having a sink basin may include obtaining a liquid dispensing and effluent shielding container assembly including a splash guard including a splash guard shield and an injection nozzle carried by the splash guard shield, the injection nozzle having an injection nozzle bore and at least one injection opening in the injection nozzle, the at least one injection opening, disposed in fluid communication with the injection nozzle bore; inserting the injection nozzle of the liquid dispensing and effluent shielding container assembly in the at least one overflow opening in the sink basin until the splash guard substantially covers the at least one overflow opening; and expelling the antimicrobial or cleaning agent liquid through the injection nozzle and the at least one injection opening and into the overflow space in the sink basin of the sink, respectively.

20 Claims, 6 Drawing Sheets

(56) References Cited

U.S. PATENT DOCUMENTS

| | | | |
|---|---|---|---|
| 8,672,904 B1* | 3/2014 | Schultz | A61M 3/0262 |
| | | | 604/302 |
| D702,124 S | 4/2014 | Harrower et al. | |
| D705,652 S | 5/2014 | Harrower et al. | |
| 2003/0230325 A1* | 12/2003 | Barcay | B08B 9/00 |
| | | | 134/146 |
| 2004/0261167 A1* | 12/2004 | Panopoulos | E04H 4/1654 |
| | | | 4/490 |
| 2008/0276366 A1 | 11/2008 | Bitowft | |
| 2011/0083707 A1* | 4/2011 | Beltran | E03C 1/306 |
| | | | 134/198 |

* cited by examiner

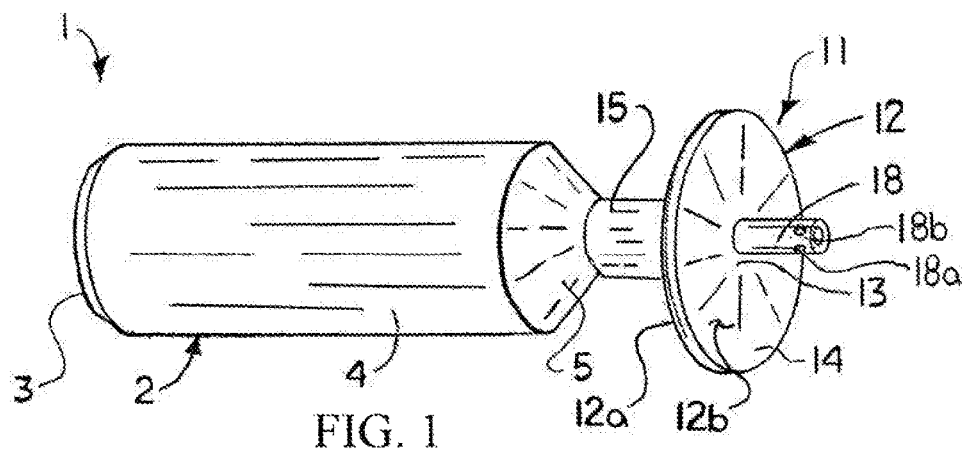
FIG. 1
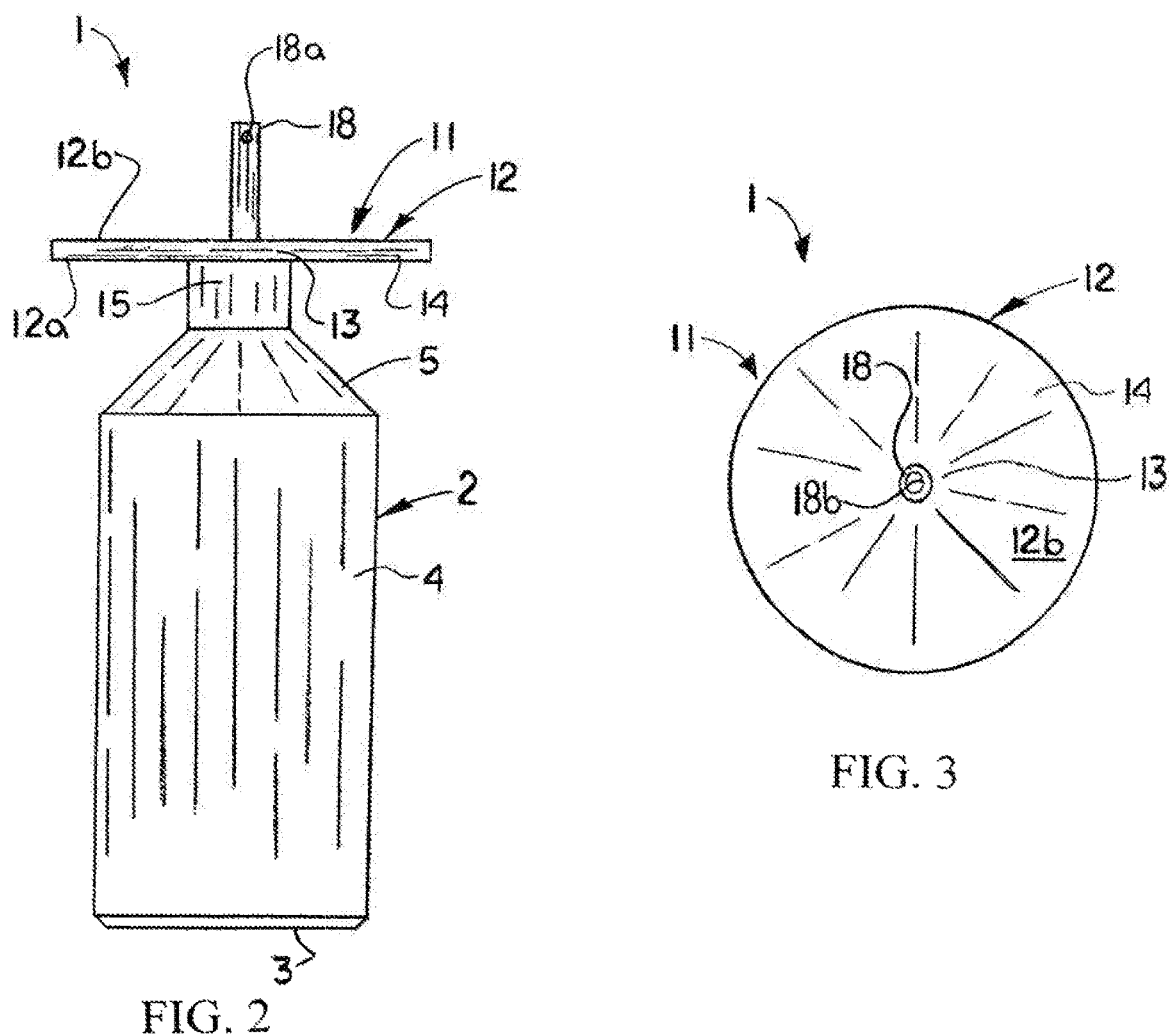
FIG. 2
FIG. 3

LIQUID-DISPENSING, EFFLUENT SHIELDING AND MICROBE ELIMINATING METHODS

CROSS-REFERENCE TO RELATED APPLICATIONS

This is a divisional of U.S. application Ser. No. 14/710,686, filed May 13, 2015 and entitled LIQUID DISPENSING AND EFFLUENT SHIELDING CONTAINER ASSEMBLIES AND MICROBE ELIMINATING METHODS, which application is hereby incorporated by reference herein in its entirety.

FIELD

Illustrative embodiments of the disclosure generally relate to containers for dispensing liquids. More particularly, illustrative embodiments of the disclosure relate to liquid dispensing, effluent shielding and microbe eliminating methods which use a liquid dispensing and effluent shielding container assembly that eliminates microbes in an overflow space in a sink by dispensing an antimicrobial liquid or cleaning agent into me overflow space through an overflow opening in the sink while substantially covering the overflow opening to prevent splash-back of effluent containing microbes into the sink.

BACKGROUND

The background description provided herein is solely for the purpose of generally presenting the context of the illustrative embodiments of the disclosure. Aspects of the background description are neither expressly nor impliedly admitted as prior art against the claimed subject matter.

Many household and commercial sinks include a sink basin having an overflow space which is built into the front or rear and bottom portions of the basin and communicates with a drain pipe. One or more overflow openings in the back wall of the sink establish communication between the interior of the basin and the overflow space. In the event that water in the basin interior rises to the level of the overflow openings, such as may occur in the event of a blockage in the basin drain, the water flows from the basin interior through the overflow opening or openings and the overflow space, respectively, and into the drain pipe to prevent the sink from overflowing.

Due to the presence of stagnant water, microbes tend to grow in the overflow space over time. These microbes may include but are not limited to bacteria such as *Stenotrophomonas maltophilia, Coryneform bacillus* and *Pseudomonas fluorescens*; fungi such as *Exophiala, Candida* and *Trichoderma*; and mold. The microbes may become a source of foul smell in the bathroom. Various approaches to eliminating the microbes in the overflow space of a sink basin may include pouring various chemicals such as bleach, mixtures of baking soda and vinegar, commercial drain cleaners and the like through the overflow opening into the overflow space. However, these substances are typically, difficult and cumbersome to pour through the overflow opening. Other solutions may include mechanical cleaning techniques which may utilize wire brushes and the like inserted from the sink basin through the overflow opening into the overflow space to scrape the microbes from the interior surfaces of the overflow space. However, these techniques are typically ineffective, messy and labor-intensive.

Accordingly, liquid dispensing, effluent shielding and microbe eliminating methods which use a liquid dispensing and effluent shielding container assembly that eliminates microbes in an overflow space in a sink by dispensing an antimicrobial liquid or liquid cleaning agent into the overflow space through an overflow opening in the sink while substantially covering the overflow opening to prevent splash-back of effluent containing microbes into the sink are needed.

SUMMARY

Illustrative embodiments of the disclosure are generally directed to methods of eliminating microbes in an overflow space in a sink having a sink basin and at least one overflow opening in the sink basin and communicating with the overflow space. An illustrative embodiment of the methods may include obtaining a liquid dispensing and effluent shielding container assembly having a flexible container with a container interior and a splash guard including a splash guard shield carried by the container and an injection nozzle carried by the splash guard shield, the injection nozzle having a injection nozzle bore disposed in fluid communication with the container interior of the container; placing an antimicrobial liquid in the container interior of the container; inserting the injection nozzle of the liquid dispensing and effluent shielding container assembly in the at least one overflow opening in the sink basin until the splash guard substantially covers the at least one overflow opening; and expelling the antimicrobial liquid or liquid cleaning agent from the container through the injection nozzle and into the overflow space in the sink basin of the sink, respectively.

BRIEF DESCRIPTION OF THE DRAWINGS

Illustrative embodiments of the disclosure will now be described, by way of example, with reference to the accompanying drawings, in which:

FIG. 1 is a front perspective view of an illustrative embodiment of the liquid dispensing and effluent shielding container assemblies;

FIG. 2 is a side view of an illustrative embodiment of the liquid dispensing, and effluent shielding container assemblies;

FIG. 3 is a front view of the illustrative liquid dispensing and effluent shielding container assembly;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description.

Figures 8, 9:
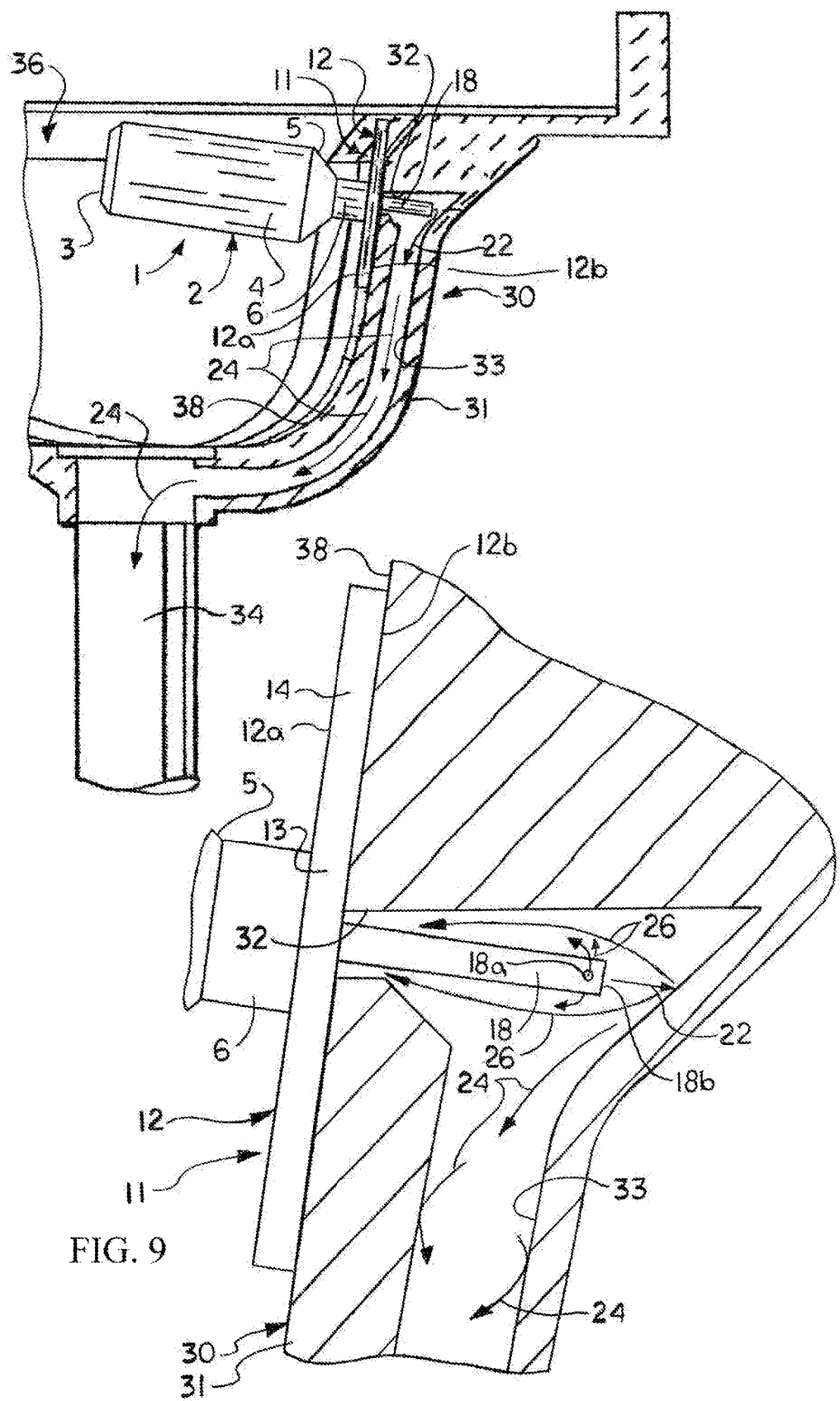
FIG. 8 is an enlarged sectional view of the sink basin, with the injection nozzle on the liquid dispensing and effluent shielding container assembly (in side view) inserted through the overflow opening into the overflow space, and more particularly illustrating injection of antimicrobial liquid or liquid cleaning agent from the injection nozzle into the overflow space to substantially eliminate microbes in the overflow space.
FIG. 9 is an enlarged sectional view of the overflow opening and the overflow space in the sink, with the injection nozzle inserted through and the splash guard substantially covering the overflow opening as antimicrobial liquid or liquid cleaning agent is injected from the injection nozzle into the overflow space and the splash guard blocking splash back of effluent from the overflow space through the overflow opening into the sink basin.

Referring initially to FIGS. 8 and 9 of the drawings, an illustrative embodiment of the liquid dispensing container assemblies, hereinafter assembly, is generally indicated by reference numeral 1. As will be hereinafter described, the assembly 1 is suitable for injecting an antimicrobial liquid or liquid cleaning agent, hereinafter liquid 22, through an overflow opening 32 in a sink basin 31 of a sink 30 to substantially eliminate microbes from an overflow space 33 in the sink basin 31. As illustrated in FIG. 9, the assembly 1 prevents splash-back 26 of microbe-containing effluent or injected liquid 24 from the overflow space 33 through the overflow opening 32 into the sink basin 31 as the liquid 22 is injected into the overflow space 33. Accordingly, the assembly 1 maintains the sanitary conditions of the sink basin 31 and protects the user while substantially eliminating the microbes from the overflow space 33. It will be recognized and understood by those skilled in the art that the assembly 1 may have uses which are not limited to those described herein, as will be apparent from a consideration of the following disclosure.

Referring next to FIGS. 1-5 of the drawings, the assembly 1 includes a flexible or squeezable container 2. The container 2 may include a container end wall 3. A flexible or squeezable container side wall 4 may extend from the container end wall 3. In some embodiments, the container side wall 4 may be generally elongated and cylindrical, as illustrated. In other embodiments, the container side wall 4 may be oval, elliptical or polygonal in cross-section. In some embodiments, a tapered container shoulder 5 may extend from the end of the container side wall 4 which is opposite the container end wall 3.

A splash guard 11 is provided on the container 2. The splash guard 11 includes a splash guard shield 12 which may be generally circular or disc-shaped in some embodiments. In other embodiments, the splash guard shield 12 may be generally elongated or may have an elliptical, rectangular or other shape. The splash guard shields 12 of different assemblies 1 may be fabricated in various shapes and sizes to sufficiently cover the overflow opening or overflow openings 32 in a variety of sinks 30 made by different manufacturers. The splash guard shield 12 may be fabricated of a soft, pliable or cushioned plastic, rubber or other material such that the splash guard shield 12 substantially conforms to the shape, contour and texture of sinks 30 (FIGS. 6-9) having a variety of sizes and shapes in application of the assembly 1.

Figure 3A:
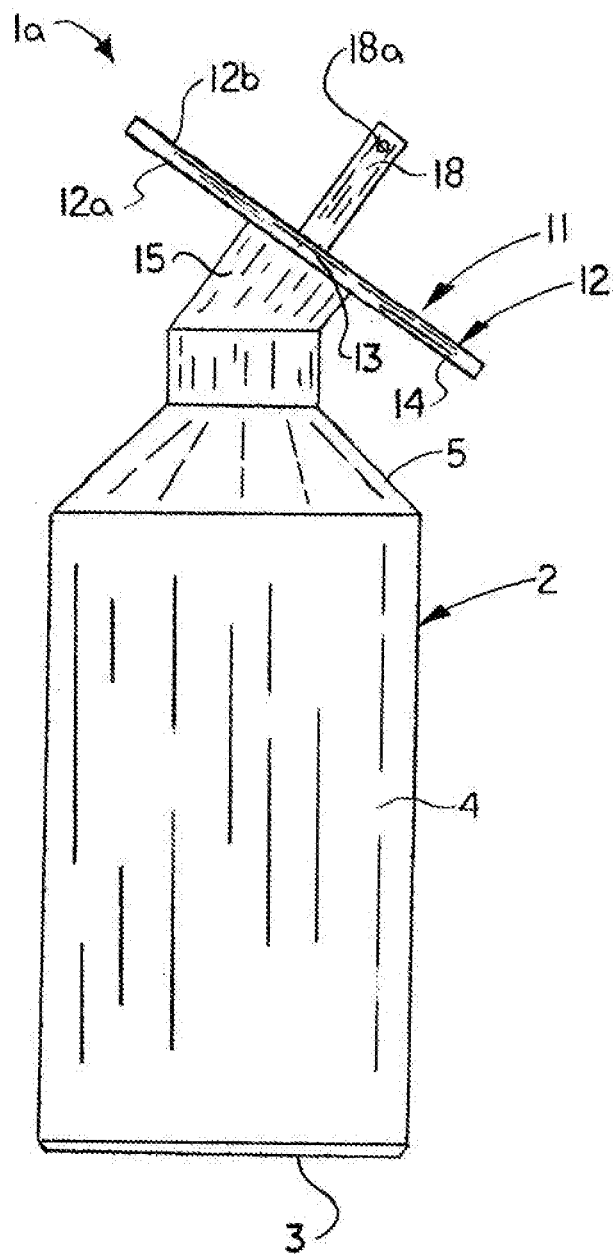
FIG. 3A is a side view of an alternative illustrative embodiment of the liquid dispensing and effluent shielding container assemblies.
Figure 5:
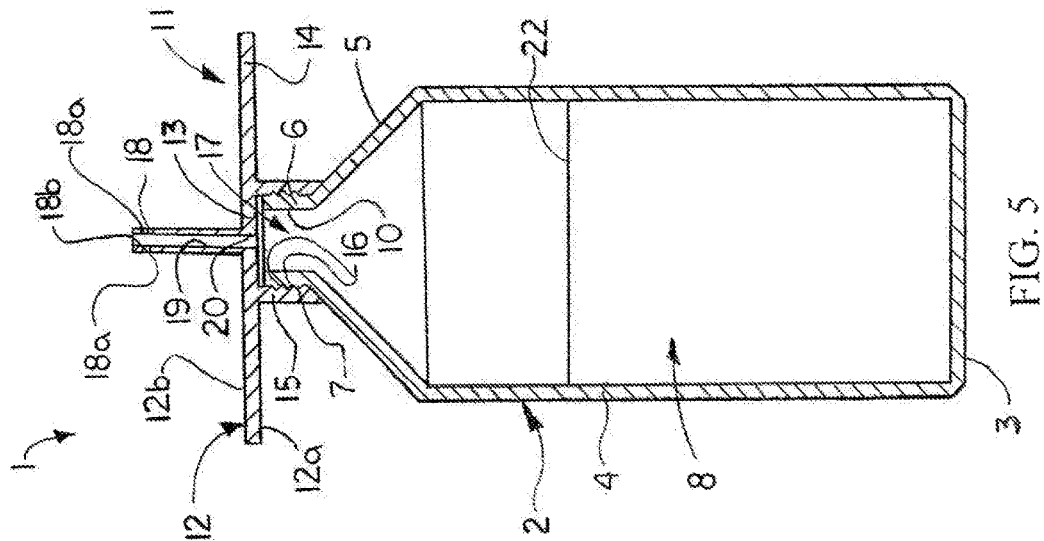
FIG. 5 is a longitudinal sectional view of the illustrative liquid dispensing and effluent shielding container assembly.
Figure 4:
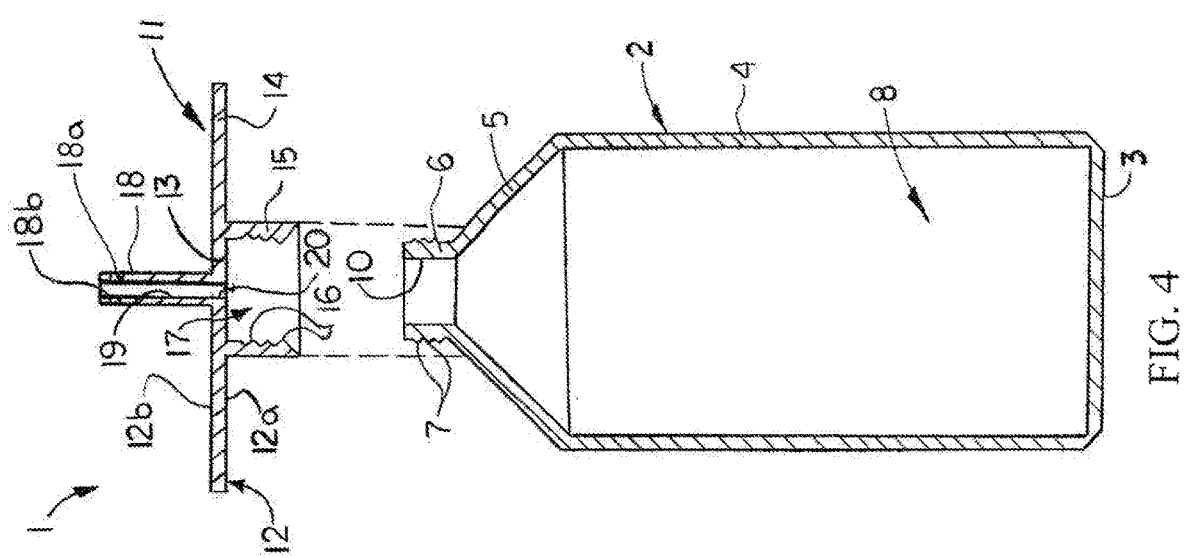
FIG. 4 is an exploded longitudinal sectional view of the illustrative liquid dispensing and effluent shielding container assembly.

The splash guard shield 12 may have a neck attachment surface 12a and a generally flat or planar aperture blocking surface 12b which is opposite the neck attachment surface 12a. As illustrated in FIGS. 4 and 5, a shield opening 20 may extend through the splash guard shield 12. A splash guard neck 15 having a neck interior 17 which communicates with the shield opening 20 may extend from the neck attachment surface 12a of the splash guard shield 12. The splash guard shield 12 may have a center shield portion 13 which spans the neck interior 17 of the splash guard neck 15 and an outer shield portion 14 which extends outwardly from the center shield portion 13 beyond the splash guard neck 15. As illustrated in FIG. 3A, in some embodiments of the assembly 1a, the splash guard neck 15 may be angled to aid in positioning of the injection nozzle 18 relative to the overflow opening 32 (FIG. 6) in the sink 30. In some embodiments, the splash guard neck 15 may be selectively adjustable to various angles according to the knowledge of those skilled in the art.

A generally elongated injection nozzle 18 may extend from the aperture blocking surface 12b of the splash guard shield 12. The injection nozzle 18 may have an injection nozzle bore 19 which communicates with the neck interior 17 of the splash guard neck 15 through the shield opening 20 in the splash guard shield 12. The injection nozzle 18 may have a longitudinal axis which is generally perpendicular to the plane of the aperture blocking surface 12b of the splash guard shield 12. At least one terminal injection opening 18b which is disposed in fluid communication with the injection nozzle bore 19 may terminate the injection nozzle 18. In some embodiments, at least one lateral injection opening 18a may be provided in a side of the injection nozzle 18 in fluid communication with the injection nozzle bore 19 to facilitate multi-directional ejection of the liquid 22 from the injection nozzle 18.

As illustrated in FIGS. 4 and 5, in some embodiments, the splash guard 11 may detachably engage the container 2 according to the knowledge of those skilled in the art. Accordingly, a container nipple 6 may protrude from the container shoulder 5 of the container 2. The container nipple 6 may have a nipple opening 10 which communicates with the container interior 8 of the container 2. The container nipple 6 may have exterior nipple threads 7. The splash guard neck 15 of the splash guard 11 may have interior neck threads 16 which detachably engage the companion exterior nipple threads 7 on the container nipple 6, as illustrated in FIG. 5, such that the injection nozzle bore 19 of the injection nozzle 18 is disposed in fluid communication with the nipple opening 10 of the container nipple 6 typically through the shield opening 20 in the splash guard shield 12. In other embodiments, the splash guard neck 15 may be fabricated in one piece with the container 2 using conventional molding and/or other manufacturing techniques known by those skilled in the art. The container 2 and the splash guard 11 of the assembly 1 may be fabricated of flexible or squeezable plastic materials such as polyethylene or polypropylene, for example and without limitation, using conventional molding and/or other fabrication techniques known by those skilled in the art.

Referring next to FIGS. 6-9 of the drawings, in typical application, the liquid dispensing container assembly 1 facilitates removal of microbes (not illustrated) such as bacteria, fungi and mold from an overflow space 33 (FIG. 7) in a sink 30. The sink 30 may be a common household sink with conventional design and having a sink basin 31 and an overflow space 33 in the front or rear and bottom portions of the sink basin 31. The sink basin 31 has a basin interior 36. At least one overflow opening 32 extends through a back wall 38 of the sink basin 31 and communicates with the overflow space 33. In some sinks 30, a single, elongated or elliptical overflow opening 32 may extend through the back wall 38 of the sink basin 31. In other sinks 30, multiple overflow openings 32 may extend through the back wall 38 of the sink basin 31 in a pattern which is selected by the sink manufacturer. A drain pipe 34 communicates with the basin interior 36 of the sink basin 31 and with the overflow space 33.

Figure 6:
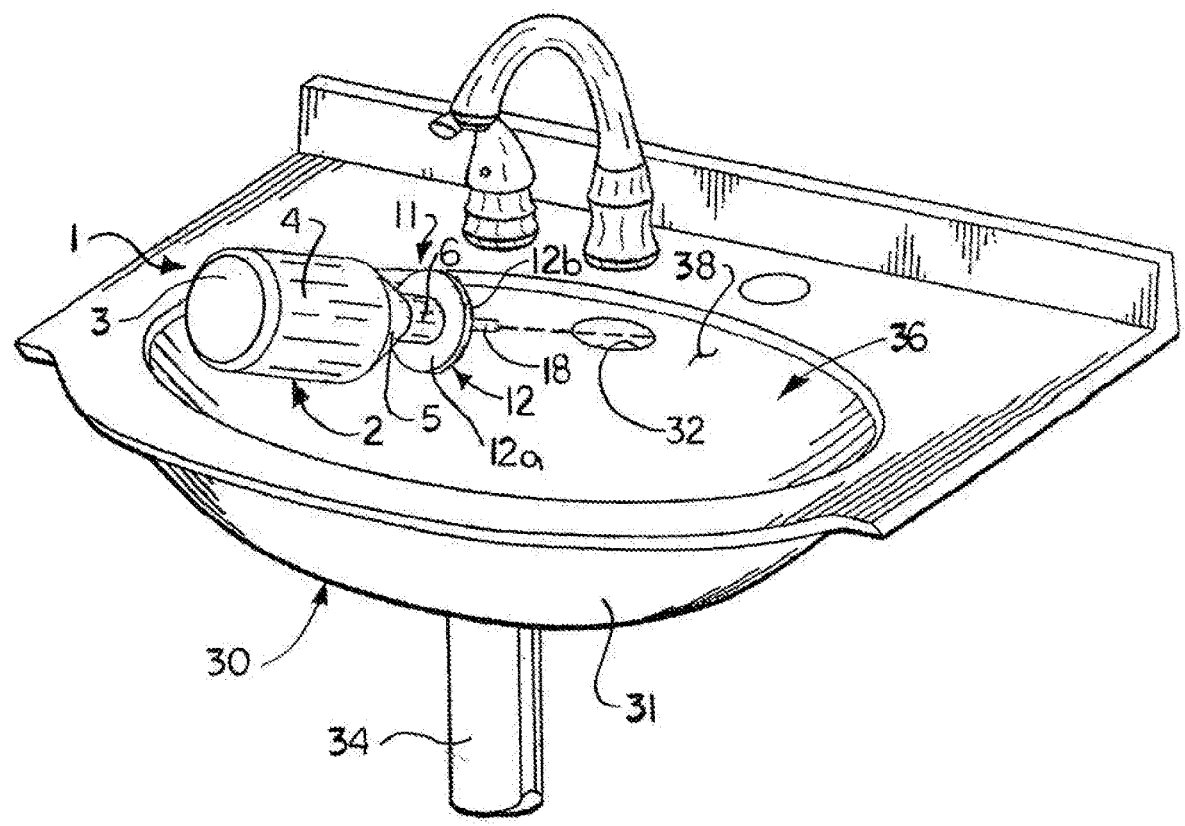
FIG. 6 is a perspective view of a sink, more particularly illustrating insertion of a injection nozzle on an illustrative liquid dispensing and effluent shielding container assembly through an overflow opening in the sink basin of the sink preparatory to injection of an antimicrobial liquid or liquid cleaning agent from the injection nozzle through the overflow opening into the overflow space, respectively, of the sink.
Figure 7:
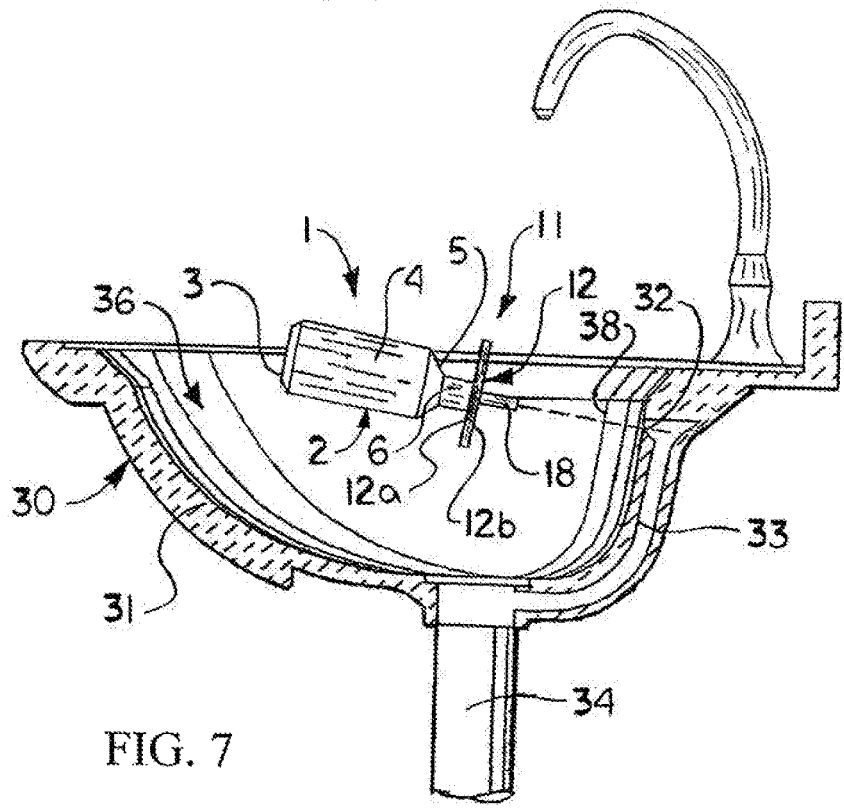
FIG. 7 is a cross-sectional view of the sink basin of a sink, more particularly illustrating insertion of a injection nozzle on an illustrative liquid dispensing and effluent shielding container assembly (in side view) into an overflow opening in the sink basin of the sink preparatory to injection of an antimicrobial liquid or liquid cleaning agent from the injection nozzle into the overflow space of the sink.

As illustrated in FIG. 5, an antimicrobial or cleaning agent liquid 22 may be placed in the container interior 8 of the container 2 typically after removal of the splash guard neck 15 of the splash guard 11 from the container nipple 6 of the container 2. Alternatively, the liquid 22 can be drawn from a storage container (not illustrated) via negative pressure through the injection nozzle 18, the shield opening 20 and the splash guard neck 15 and into the container interior 8 of the container 2, respectively, by squeezing and releasing the container 2. The liquid 22 may include bleach such as CLOROX®, for example and without limitation, and may additionally include antimicrobial agents or liquids. As illustrated in FIGS. 6 and 7, the liquid dispensing container assembly 1 is next oriented in the basin interior 36 such that the injection nozzle 18 of the splash guard 11 registers with one of the overflow openings 32 in the sink basin 31. As illustrated in FIGS. 8 and 9, the injection nozzle 18 is inserted through the overflow opening 32 until the aperture blocking surface 12b of the splash guard shield 12 engages the rear wall 38 of the sink basin 31 in the basin interior 36 and substantially covers the overflow opening or openings 32. Next, the container 2 is squeezed to force or eject the liquid 22 from the container interior 8 (FIGS. 4 and 5) through the nipple opening 10 of the container nipple 6, the splash guard opening 20 in the splash guard shield 12 and the injection nozzle bore 19 of the injection nozzle 18, respectively, and into the overflow space 33 of the sink basin 31. As illustrated in FIG. 9, the liquid 22 may additionally be ejected laterally from the injection nozzle 18 through the lateral injection openings 18a into the overflow space 33. Accordingly, as further illustrated in FIGS. 8 and 9, the flowing liquid 22 contacts the interior surfaces of the overflow space 33 and contacts, kills and dislodges or substantially removes the microbes growing on the interior surfaces of the overflow space 33. The resulting effluent 24, which includes the liquid 22 and killed and dislodged microbes, flows from the overflow space 33 into the drain pipe 34. As illustrated in FIG. 9, it will be appreciated by those skilled in the art that effluent splash back 26 of the effluent 24 may otherwise have a tendency to be ejected from the interior surfaces of the overflow space 33 and back through the overflow opening or openings 32 into the basin interior 36 of the sink basin 31. However, the splash guard shield 12 of the splash guard 11 on the assembly 1 blocks the overflow opening or openings 32 and prevents the effluent splash back 26 or injected liquid 22 from being ejected from the interior surfaces of the overflow space 33 through the overflow opening 32 into the basin interior 36. Therefore, the splash guard 11 facilitates sanitary killing and removal of the microbes from the overflow space 33 and prevents the effluent 24 which may contain microbes from contaminating the basin interior 36 of the sink basin 31 and protects the user of the assembly 1.

After use, the injection nozzle 18 is withdrawn from the overflow opening 32 as the aperture blocking surface 12b of the splash guard shield 12 disengages the rear wall 38 of the sink basin 31 and uncovers the overflow opening or openings 32. In some embodiments, the splash guard 11 may be removed from the container 2 typically by unthreading the interior neck threads 16 (FIGS. 4 and 5) in the splash guard neck 15 from the companion exterior nipple threads 7 on the container nipple 6. The container 2 can be washed and a replacement supply of liquid 22 placed in the container interior 8 for subsequent use. The splash guard 11 can likewise be cleaned and replaced back on the container 2 prior to use.

Figure 10:
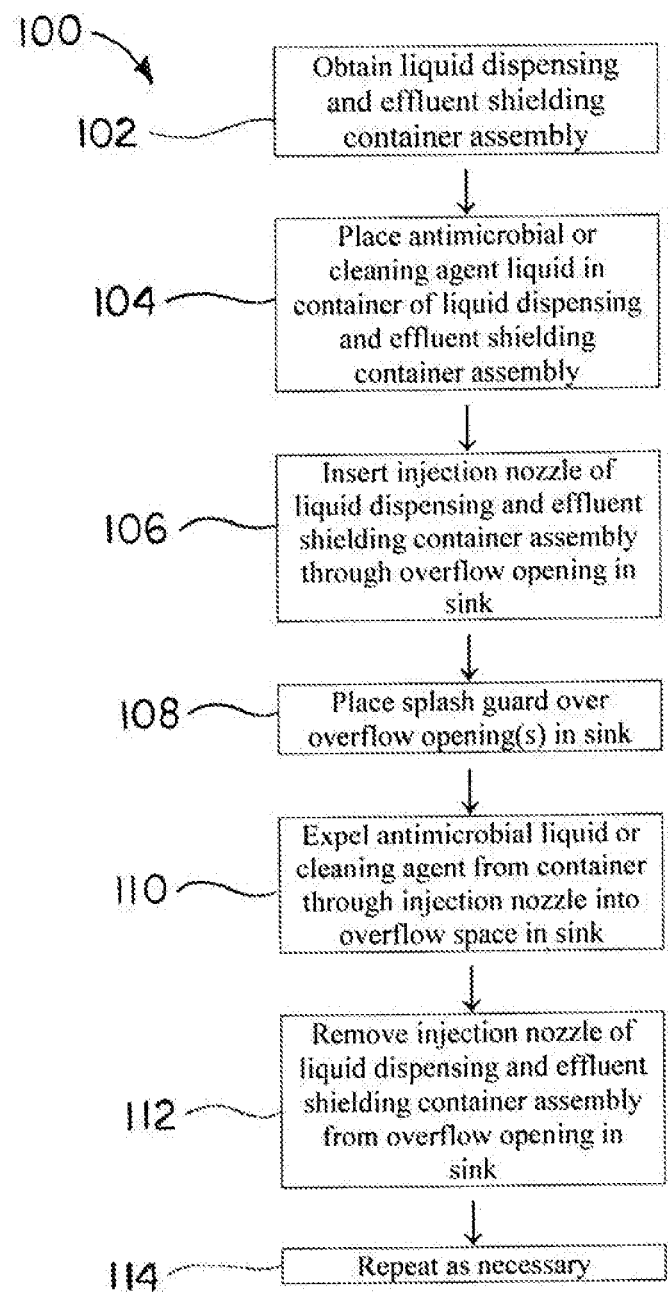
FIG. 10 is a flow diagram of an illustrative embodiment of a method of eliminating microbes in an overflow space in a sink.

Referring next to FIG. 10 of the drawings, an illustrative embodiment of a method of substantially eliminating microbes in an overflow space in a sink basin is generally indicated by reference numeral 100. At Step 102, a liquid dispensing and effluent shielding container assembly is obtained. The liquid dispensing and effluent shielding container assembly may include a flexible container having a container interior and a splash guard including a splash guard shield carried by the container and an injection nozzle carried by the splash guard shield. The injection nozzle may have an injection nozzle bore disposed in fluid communication with the container interior of the container. At Step 104, antimicrobial liquid or cleaning agent may be placed in the container interior of the container of the liquid dispensing and effluent shielding container assembly. At Step 106, the injection nozzle of the liquid dispensing and effluent shielding container assembly may be inserted through an overflow opening in the sink. At Step 108, the splash guard of the assembly may be placed over the overflow opening or openings in the sink to substantially cover or block the overflow opening or openings. At Step 110, the antimicrobial liquid or cleaning agent may be expelled from the container through the injection nozzle into the overflow space in the sink. At Step 112, the injection nozzle of the liquid dispensing and effluent shielding container assembly may be removed from the overflow opening in the sink. At Step 114, the process may be repeated as necessary to substantially eliminate the microbes in the overflow space in the sink basin.

While illustrative embodiments of the disclosure have been described above, it will be recognized and understood that various modifications can be made and the appended claims are intended to cover all such modifications which may fall within the spirit and scope of the disclosure.

What is claimed is:

1. A method of eliminating microbes in an overflow space in a sink having a sink basin and at least one overflow opening in the sink basin and communicating with the overflow space, the method comprising:

obtaining a liquid dispensing and effluent shielding container assembly including a flexible container having a container interior and a splash guard including a substantially flat or planar splash guard shield carried by the container, the splash guard shield having an aperture blocking surface and a shield edge circumscribing, the aperture blocking surface, the aperture blocking surface configured for substantially uniform and complete, flat engagement with the sink basin in substantially covering relationship to the at least one overflow opening, and an injection nozzle carried by the splash guard shield and protruding beyond the aperture blocking surface, the injection nozzle having an injection nozzle bore disposed in fluid communication with the container interior of the container and at least one injection opening in the injection nozzle, the at least one injection opening disposed in fluid communication with the injection nozzle bore, the aperture blocking surface having a constant planar contour from the shield edge to the injection nozzle;

placing an antimicrobial or c caning agent liquid in the container interior of the container;

inserting the injection nozzle of the liquid dispensing and effluent shielding container assembly in the at least one overflow opening in the sink basin until the aperture blocking surface on the splash guard shield of the splash guard substantially uniformly, completely and flatly engages the sink basin and covers the at least one overflow opening; and expelling the antimicrobial or cleaning agent liquid from the container through the injection nozzle and the at least one injection opening and into the overflow space in the sink basin of the sink, respectively.

2. The method of claim 1 wherein placing the antimicrobial liquid in the container interior of the container comprises placing bleach with antimicrobial agent in the container interior of the container.

3. The method of claim 1 wherein obtaining the liquid dispensing and effluent shielding container assembly comprises obtaining the liquid dispensing and effluent shielding container assembly including a flexible, generally cylindrical container side wall and a container end wall carried by the container side wall with the splash guard shield of the splash guard carried by the container side wall opposite the container end wall.

4. The method of claim 1 wherein obtaining the liquid dispensing and effluent shielding container assembly comprises obtaining the liquid dispensing and effluent shielding container assembly including a tapered container shoulder extending from the container side wall opposite the container end wall and a splash guard neck of the splash guard, carried by the container shoulder, with the splash guard shield carried by the splash guard neck.

5. The method of claim 1 wherein obtaining the liquid dispensing and effluent shielding container assembly comprises obtaining the liquid dispensing and effluent shielding container assembly including a container nipple carried by the container side wall opposite the container end wall and a splash guard neck of the splash guard detachably engaging the container nipple, with the splash guard shield carried by the splash guard neck.

6. The method of claim 1 wherein obtaining, the liquid dispensing and effluent shielding container assembly comprises obtaining the liquid dispensing and effluent shielding container assembly including a container nipple carried by the container side wall and a splash guard neck of the splash guard threadably engaging the container nipple the splash guard neck.

7. The method of claim 1 wherein obtaining the liquid dispensing and effluent shielding container assembly including the injection nozzle having at least one injection opening in the injection nozzle comprises obtaining the liquid dispensing and effluent shielding container assembly including at least one terminal injection opening disposed in fluid communication with the injection nozzle bore, and wherein expelling the antimicrobial or cleaning agent liquid from the container through the injection nozzle and the at least one injection opening comprises expelling the antimicrobial or cleaning agent from the container through the injection nozzle and the at least one terminal injection opening and into the overflow space in the sink basin of the sink, respectively.

8. The method of claim 1 wherein obtaining the liquid dispensing and effluent shielding container assembly including the injection nozzle having at least one injection opening in the injection nozzle comprises obtaining the liquid dispensing and effluent shielding container assembly including at least one lateral injection opening disposed in fluid communication with the injection nozzle bore, and wherein expel line the antimicrobial or cleaning agent liquid from the container through the injection nozzle and the at least one injection opening comprises expelling the antimicrobial or cleaning agent from the container through the injection nozzle and the at least one lateral injection opening and into the overflow space in the sink basin of the sink, respectively.

9. A method of eliminating microbes in an overflow space in a sink having a sink basin and at least one overflow opening in the sink basin and communicating with the overflow space, the method comprising:

obtaining a liquid dispensing and effluent shielding container assembly including a flexible container having a container interior and a splash guard including a substantially flat or planar splash guard shield carried by the container, the splash guard shield having a neck attachment surface, an aperture blocking surface, a shield edge circumscribing the aperture blocking surface, the aperture blocking surface configured for substantially uniform and complete, flat engagement with the sink basin in substantially covering relationship to the at least one overflow opening, and a shield opening extending through the splash guard shield from the neck attachment surface to the aperture blocking surface, an injection nozzle carried by the aperture blocking surface of the splash guard shield, the injection nozzle having an injection nozzle bore disposed in fluid communication with the container interior of the container through the shield opening and at least one it opening in the injection nozzle, the at least one injection opening disposed in fluid communication with the injection nozzle bore, the aperture blocking surface having a constant planar contour from the shield edge to the injection nozzle;

placing an antimicrobial or cleaning agent liquid in the container interior of the container;

inserting the injection nozzle of the liquid dispensing and effluent shielding container assembly in the at least one overflow opening in the sink basin until the aperture blocking surface on the splash guard shield of the splash guard substantially uniformly and completely and flatly engages the sink basin and covers the at least one overflow opening; and expelling the antimicrobial or cleaning agent liquid from the container through shield opening, the injection nozzle and the at least one injection opening, respectively, and into the overflow space in the sink basin of the sink.

10. The method of claim 9 wherein placing, the antimicrobial liquid in the container interior of the container comprises placing bleach with antimicrobial agent in the container interior of the container.

11. The method of claim 9 wherein obtaining the liquid dispensing and effluent shielding container assembly comprises obtaining the liquid dispensing and effluent shielding container assembly including a flexible, generally cylindrical container side wall and a container end wall carried by the container side wall with the splash guard shield of the splash guard carried by the container side wall opposite the container end wall.

12. The method of claim 9 wherein obtaining the liquid dispensing and effluent shielding container assembly comprises obtaining the liquid dispensing and effluent shielding container assembly including a tapered container shoulder extending from the container side wall opposite the container end wall and a splash guard neck of the splash guard carried by the container shoulder, with the splash guard shield carried by the splash guard neck.

13. The method of claim 9 wherein obtaining the liquid dispensing and effluent shielding container assembly comprises obtaining the liquid dispensing and effluent shielding container assembly including a container nipple carried by the container side wall opposite the container end wall and a splash guard neck of the splash guard detachably engaging the container nipple, with the splash guard shield carried by the splash guard neck.

14. The method of claim 9 wherein obtaining the liquid dispensing and effluent shielding container assembly comprises obtaining the liquid dispensing and effluent shielding container assembly including a container nipple carried by the container side wall and a splash guard neck of the splash guard threadably engaging the container nipple the splash guard neck.

15. The method of claim 9 wherein obtaining the liquid dispensing and effluent shielding container assembly including the injection nozzle having at least one injection opening in the injection nozzle comprises obtaining the liquid dispensing and effluent shielding container assembly including at least one terminal injection opening disposed in fluid communication with the injection nozzle bore, and wherein expelling the antimicrobial or cleaning agent liquid from the container through the injection nozzle and the at least one injection opening comprises expelling the antimicrobial or cleaning agent from the container through the injection nozzle and the at least one terminal injection opening and into the overflow space in the sink basin of the sink, respectively.

16. The method of claim 9 wherein obtaining the liquid dispensing and effluent shielding container assembly including the injection nozzle having at least one injection opening in the injection nozzle comprises obtaining the liquid dispensing and effluent shielding container assembly including at least one lateral injection opening disposed in fluid communication with the injection nozzle bore, and wherein expelling the antimicrobial or cleaning agent liquid from the container through the injection nozzle and the at least one injection opening comprises expelling the antimicrobial or cleaning agent from the container through the injection nozzle and the at least one lateral injection opening and into the overflow space in the sink basin of the sink, respectively.

17. A method of eliminating microbes in an overflow space in a sink having a sink basin and at least one overflow opening in the sink basin and communicating with the overflow space, the method comprising:

obtaining a liquid dispensing and effluent shielding container assembly including a flexible container having a container interior and a splash guard including a substantially flat or planar splash guard shield carried by the container, the splash guard shield having a neck attachment surface, an aperture blocking surface, a shield edge circumscribing the aperture blocking surface, the aperture blocking surface configured for substantially uniform and complete, flat engagement with the sink basin in substantially covering relationship to the at least one overflow opening, a shield edge circumscribing the aperture blocking surface and a shield opening extending through the splash guard shield from the neck attachment surface to the aperture blocking surface, the aperture blocking surface configured for substantially uniform and complete engagement with the sink basin in substantially covering relationship to the at least one overflow opening, an injection nozzle carried by the aperture blocking surface of the splash guard shield and protruding beyond the aperture blocking surface, the injection nozzle having an injection nozzle bore disposed in fluid communication with the container interior of the container through the shield opening and at least one injection opening in the injection nozzle, the at least one injection opening disposed in fluid communication with the injection nozzle bore, the aperture blocking surface having a constant planar contour from the shield edge to the injection nozzle;

placing an antimicrobial or cleaning agent liquid in the container interior of the container;

inserting the injection nozzle of the liquid dispensing and effluent shielding container assembly in the at least one overflow opening in the sink basin until the aperture blocking surface on the splash guard shield of the splash guard substantially uniformly, completely and flatly engages the sink basin and covers the at least one overflow opening;

placing the splash guard over the at least one Overflow opening in the sink basin; and expelling the antimicrobial or cleaning agent liquid from the container through shield opening, the injection nozzle and the at least one injection opening, respectively, and into the overflow space in the sink basin of the sink.

18. The method of claim 17 wherein placing the antimicrobial liquid in the container interior of the container comprises placing bleach with antimicrobial agent in the container interior of the container.

19. The method of claim 17 wherein obtaining the liquid dispensing and effluent shielding container assembly including the injection nozzle having at least one injection opening in the injection nozzle comprises obtaining the liquid dispensing and effluent shielding container assembly including at least one terminal injection opening disposed in fluid communication with the injection nozzle bore, and wherein expelling the antimicrobial or cleaning agent liquid from the container through the injection nozzle and the at least one injection opening comprises expelling the antimicrobial or cleaning agent from the container through the injection nozzle and the at least one terminal injection opening and into the overflow space in the sink basin of the sink, respectively.

20. The method of claim 17 wherein obtaining the liquid dispensing and effluent shielding container assembly including the injection nozzle having at least one injection opening in the injection nozzle comprises obtaining the liquid dispensing and effluent shielding container assembly including at least one lateral injection opening disposed in fluid communication with the injection nozzle bore, and wherein expelling the antimicrobial or cleaning agent liquid from the container through the injection nozzle and the at least one injection opening comprises expelling the antimicrobial or cleaning agent from the container through the injection nozzle and the at least one lateral injection opening and into the overflow space in the sink basin of the sink, respectively.

\* \* \* \* \*